United States Patent
Yang

(10) Patent No.: US 11,234,672 B2
(45) Date of Patent: Feb. 1, 2022

(54) ULTRASONIC IMAGING APPARATUS AND METHOD FOR CONTROLLING THE SAME

(71) Applicant: SAMSUNG MEDISON CO., LTD., Gangwon-do (KR)

(72) Inventor: Sun-Mo Yang, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 1209 days.

(21) Appl. No.: 15/461,163

(22) Filed: Mar. 16, 2017

(65) Prior Publication Data

US 2018/0070914 A1    Mar. 15, 2018

(30) Foreign Application Priority Data

Sep. 12, 2016    (KR) .................. 10-2016-0117054

(51) Int. Cl.
*A61B 8/08*    (2006.01)
*A61B 8/00*    (2006.01)

(52) U.S. Cl.
CPC ............... *A61B 8/08* (2013.01); *A61B 8/085* (2013.01); *A61B 8/4405* (2013.01); *A61B 8/463* (2013.01); *A61B 8/469* (2013.01); *A61B 8/485* (2013.01); *A61B 8/52* (2013.01); *A61B 8/5246* (2013.01); *A61B 8/565* (2013.01); *A61B 8/4427* (2013.01); *A61B 8/4472* (2013.01); *A61B 8/4494* (2013.01); *A61B 8/465* (2013.01); *A61B 8/486* (2013.01); *A61B 8/488* (2013.01)

(58) Field of Classification Search
CPC ......... A61B 8/08; A61B 8/085; A61B 8/4405; A61B 8/4427; A61B 8/4472; A61B 8/485; A61B 8/5207; A61B 8/5223; G01S 15/8993; G01S 7/52022
See application file for complete search history.

(56) References Cited

U.S. PATENT DOCUMENTS

| 2012/0136250 A1* | 5/2012 | Tabaru ................ G01S 7/52026 |
|---|---|---|
| | | 600/438 |
| 2013/0028536 A1* | 1/2013 | Hazard ................ A61B 8/5276 |
| | | 382/275 |

(Continued)

FOREIGN PATENT DOCUMENTS

| JP | 2006-141508 A | 6/2006 |
|---|---|---|
| JP | 2009-261493 A | 11/2009 |
| JP | 2011-115456 A | 6/2011 |

OTHER PUBLICATIONS

Office Action issued in corresponding European Application No. 17 162 670.8, dated Apr. 25, 2019.

*Primary Examiner* — Baisakhi Roy
(74) *Attorney, Agent, or Firm* — Morgan, Lewis & Bockius LLP

(57) ABSTRACT

An ultrasonic imaging apparatus and a method for controlling the same are disclosed. The ultrasonic imaging apparatus includes: an ultrasonic probe configured to acquire a plurality of shear wave data segments from a target object; a controller configured to determine at least one shear wave data group by grouping the plurality of shear wave data segments according to a predetermined condition; and a display configured to display at least one image corresponding to the at least one shear wave data group, and display the plurality of shear wave data segments at positions different from a specific position at which the image is displayed.

15 Claims, 13 Drawing Sheets

(56) References Cited

U.S. PATENT DOCUMENTS

| | | | | |
|---|---|---|---|---|
| 2014/0046173 A1* | 2/2014 | Greenleaf | G16H 50/30 | |
| | | | | 600/411 |
| 2014/0243668 A1* | 8/2014 | Varghese | G01S 7/52042 | |
| | | | | 600/438 |
| 2015/0080730 A1* | 3/2015 | Kanayama | G01S 7/52042 | |
| | | | | 600/447 |
| 2015/0087976 A1* | 3/2015 | Fan | A61B 8/5207 | |
| | | | | 600/438 |
| 2015/0209013 A1* | 7/2015 | Tsymbalenko | A61B 8/483 | |
| | | | | 600/440 |
| 2016/0183926 A1* | 6/2016 | Asami | A61B 8/5207 | |
| | | | | 600/438 |
| 2017/0322308 A1* | 11/2017 | Loupas | A61B 8/08 | |

* cited by examiner

ULTRASONIC IMAGING APPARATUS AND METHOD FOR CONTROLLING THE SAME

CROSS-REFERENCE TO RELATED APPLICATION

This application claims the benefit of Korean Patent Application No. 2016-0117054, filed on Sep. 12, 2016 in the Korean Intellectual Property Office, the disclosure of which is incorporated herein by reference.

BACKGROUND

1. Field

Embodiments of the present disclosure relate to an ultrasonic imaging apparatus and a method for controlling the same.

2. Description of the Related Art

An ultrasonic diagnostic apparatus applies an ultrasonic signal from the surface of an object (for example, a human body) to a target site inside of the body of the object, and non-invasively acquires tomograms of soft tissues or images regarding blood flow upon receiving reflected echo signals.

The ultrasonic diagnostic apparatus has compact size and low price, displays a diagnostic image in real time, as compared to other image diagnostic apparatuses, for example, an X-ray diagnostic apparatus, a computed tomography (CT) scanner, a magnetic resonance imaging (MRI) apparatus, and a nuclear medical diagnostic apparatus. In addition, since the ultrasonic diagnostic apparatus does not cause radiation exposure, the ultrasonic diagnostic apparatus is inherently safe. Accordingly, the ultrasonic diagnostic apparatus has been widely utilized for cardiac, abdominal, and urologic diagnosis as well as obstetric and gynecological diagnosis.

The ultrasonic diagnostic apparatus includes an ultrasonic probe for transmitting ultrasonic signals to a target object so as to acquire an ultrasonic image of the target object, and receiving ultrasonic echo signals reflected from the target object.

In recent times, most of the ultrasonic imaging apparatuses include a display configured to output ultrasonic images and diagnostic data regarding the ultrasonic images, and the display outputs shear wave data acquired from the ultrasonic probe.

SUMMARY

Therefore, it is an aspect of the present disclosure to provide an ultrasonic imaging apparatus for grouping a plurality of shear wave data segments according to a predetermined condition and classifying the plurality of shear wave data segments into at least one shear wave data group, and a method for controlling the same.

It is another aspect of the present disclosure to provide an ultrasonic imaging apparatus for displaying at least one image corresponding to at least one shear wave data group, and a method for controlling the same.

In accordance with one aspect of the present disclosure, an ultrasonic imaging apparatus includes: an ultrasonic probe configured to acquire a plurality of shear wave data segments from a target object; a controller configured to determine at least one shear wave data group by grouping the plurality of shear wave data segments according to a predetermined condition; and a display configured to display at least one image corresponding to the at least one shear wave data group, and display the plurality of shear wave data segments at positions different from a specific position at which the image is displayed.

The display may selectively display the at least one image corresponding to the at least one shear wave data group.

The predetermined condition may include at least one of a Region of Interest (ROI) region, a target site, an image range, an image type, and an image position.

The controller may allow the plurality of shear wave data segments to satisfy a predetermined condition, may group the plurality of shear wave data segments according to a user manipulation or a predefined instruction, and may thus determine the at least one shear wave data group.

The at least one image may be visually distinguished from each other using at least one of a symbol, a letter, a figure, a shape, a color, and a solid structure.

The ultrasonic imaging apparatus may further include: an input portion configured to select the at least one image corresponding to the at least one shear wave data group.

If the at least one image corresponding to the at least one shear wave data group is selected through the input portion, the display may rearrange the plurality of shear wave data segments belonging to the selected image, and may display the rearranged shear wave data segments.

The ultrasonic imaging apparatus may further include a communicator configured to transmit information needed to display the at least one image corresponding to the at least one shear wave data group to an external device.

The ultrasonic imaging apparatus may further include: if the at least one image corresponding to the at least one shear wave data group is selected through the input portion, a notification portion is configured to inform a user of the selection result.

In accordance with another aspect of the present disclosure, a method for controlling an ultrasonic imaging apparatus includes: acquiring a plurality of shear wave data segments from a target object; determining at least one shear wave data group by grouping the plurality of shear wave data segments according to a predetermined condition; and displaying at least one image corresponding to the at least one shear wave data group, and displaying the plurality of shear wave data segments at positions different from a specific position at which the image is displayed.

The displaying may include: selectively displaying the at least one image corresponding to the at least one shear wave data group.

The predetermined condition may include at least one of a Region of Interest (ROI) region, a target site, an image range, an image type, and an image position.

The determining the at least one shear wave data group may include: allowing the plurality of shear wave data segments to satisfy a predetermined condition, grouping the plurality of shear wave data segments according to a user manipulation or a predefined instruction, and thus determining the at least one shear wave data group.

The at least one image may be visually distinguished from each other using at least one of a symbol, a letter, a figure, a shape, a color, and a solid structure.

The method may further include: selecting the at least one image corresponding to the at least one shear wave data group.

The displaying may include: if the at least one image corresponding to the at least one shear wave data group is selected, rearranging the plurality of shear wave data segments belonging to the selected image, and displaying the rearranged shear wave data segments.

The method may further include: transmitting information needed to display the at least one image corresponding to the at least one shear wave data group to an external device.

The method may further include: if the at least one image corresponding to the at least one shear wave data group is selected, informing a user of the selection result.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Hereinafter, the above and other objects, specific advantages, and novel features of the present invention will become apparent from the following description of embodiments, given in conjunction with the accompanying drawings. Reference will now be made in detail to the embodiments of the present invention, examples of which are illustrated in the accompanying drawings. Wherever possible, the same reference numbers will be used throughout the drawings to refer to the same or like parts. In the following description, known functions or structures, which may confuse the substance of the present invention, are not explained. It will be understood that, although the terms first, second, etc. may be used herein to describe various elements, components, regions, layers and/or sections, these elements, components, regions, layers and/or sections should not be limited by these terms.

An ultrasonic probe, an ultrasonic imaging apparatus and a method for controlling the same according to the embodiments of the present disclosure will hereinafter be given with reference to FIGS. 1 to 13.

Figure 1:
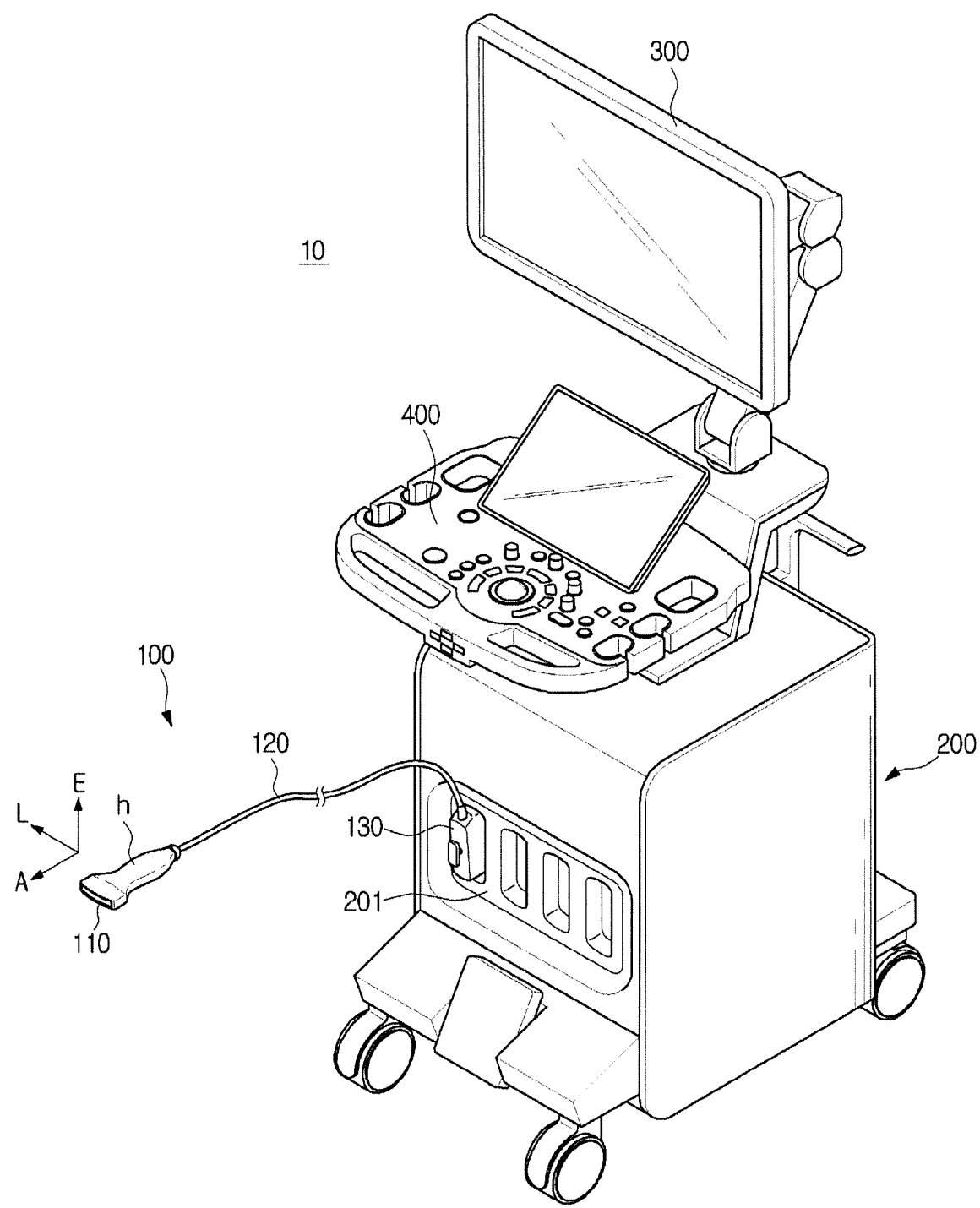
FIG. 1 is a perspective view illustrating an external appearance of an ultrasonic imaging apparatus according to an embodiment of the present disclosure.
Figure 2:
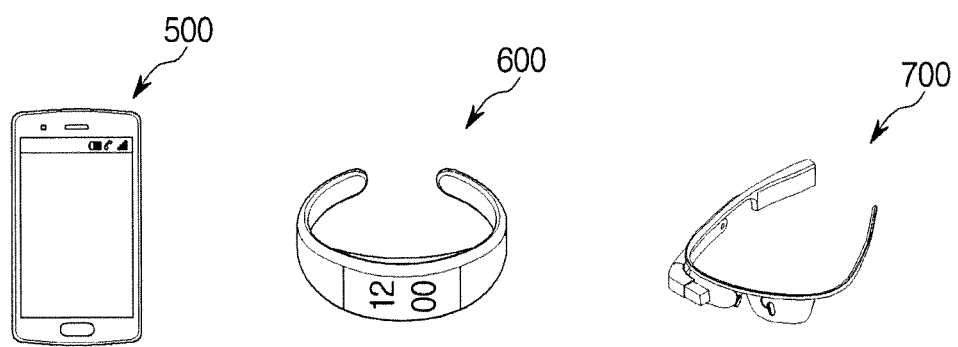
FIG. 2 is a view illustrating external devices configured to wirelessly communicate with the ultrasonic imaging apparatus.

FIG. 1 is a perspective view illustrating an external appearance of an ultrasonic imaging apparatus according to an embodiment of the present disclosure. FIG. 2 is a view illustrating external devices configured to wirelessly communicate with the ultrasonic imaging apparatus.

Referring to FIG. 1, the ultrasonic imaging apparatus 10 may include an ultrasonic probe 100 and a main body 200. The ultrasonic probe 100 may transmit an ultrasonic signal to a target object, may receive an echo ultrasonic signal from the target object, and may convert the received echo ultrasonic signal into an electrical signal to obtain an ultrasonic image. The main body 200 may generate an ultrasonic image on the basis of the ultrasonic signal. The main body 200 may be connected to the ultrasonic probe 100 over a wireless communication network or a wired communication network. The main body 200 may be a workstation including a display 300 and an input portion 400.

Figure 8:
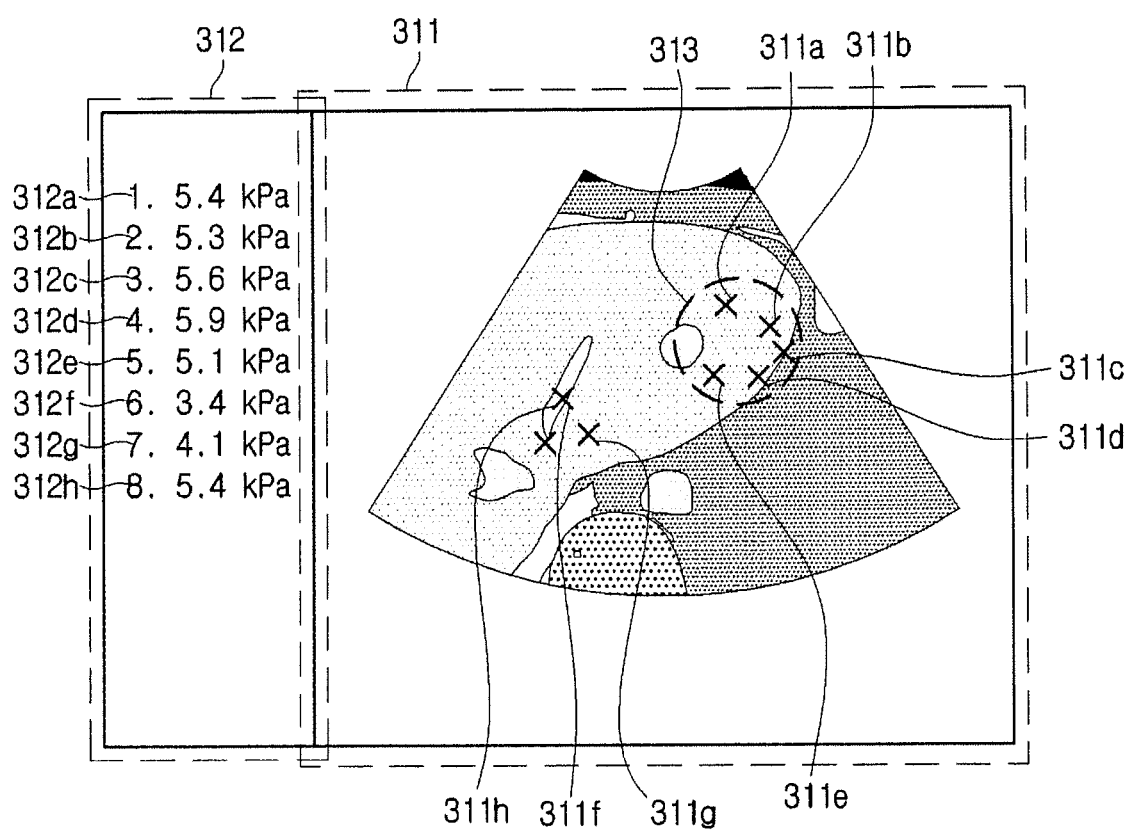
FIG. 8 is a view illustrating an example of an output screen image of the display for explaining a process for grouping a plurality of shear wave data segments.

The main body 200 may transmit and receive various kinds of information to and from an external device over a wired or wireless communication network. The external device may denote a device including a display for displaying information and a communication module for implementing wireless communication, and may be all kinds of devices capable of communicating with the ultrasonic imaging apparatus 10. The external device 300 may be implemented as any one of a laptop, a desktop computer, and a tablet PC, or may be implemented as a smartphone as shown in FIG. 8. For example, as shown in FIG. 2, the external device may be any of a smartphone 500, a PDA, a tablet PC, a personal computer (PC), a watch detachably coupled to a user's body, and glasses-type wearable terminals 600 and 700.

The ultrasonic imaging apparatus 10 may be used for ultrasonic diagnosis in hospitals or the like as shown in FIG. 1. However, the scope or spirit of the ultrasonic imaging apparatus 10 is not limited to FIG. 1.

For example, the ultrasonic imaging apparatus 10 may be implemented as any one of a laptop, a desktop computer, and a tablet PC, or may be implemented as a smartphone 500 as shown in FIG. 2. The ultrasonic imaging apparatus 10 may include a mobile terminal such as a PDA, a watch 600 detachably coupled to the user's body, and a glasses-type wearable terminal 700.

However, the ultrasonic imaging apparatus 10 is not limited thereto, and may include any device which includes a communicator therein so as to communicate with the external device over the wireless communication network and may display ultrasonic images through a display without departing from the scope or spirit of the present disclosure.

In recent times, systems (such as a Computer Aided Diagnosis (CAD) system) for primarily discriminating medical images (e.g., ultrasonic images, MRI (Magnetic Resonance Imaging) images, CT (Computed Tomography) images, etc.) to provide doctors with the presence or absence of abnormal tissues and the position of abnormal tissues have been widely used. The above-mentioned system may process information regarding the presence or absence of abnormal tissues in a medical image such as an ultrasonic image, the size of abnormal tissues, the position of abnormal tissues, etc. using a computer, may detect the abnormal tissues, may provide doctors with the detection result, and may assist image diagnosis of the doctors.

The ultrasonic imaging apparatus 10 according to this embodiment may be used to analyze elasticity of a target object. Ultrasound elastography technology may analyze the degree of elasticity of tissues, may discriminate a difference in stiffness between a normal tissue and an abnormal tissue, and may thus allow doctors to diagnose a disease. Specifically, a method for analyzing elasticity of tissues using the ultrasonic imaging apparatus 10 according to the embodiment may recognize the presence or absence of abnormal tissues such as a cancer or tumor by analyzing elasticity of tissues using ultrasonic signals generated from the ultrasonic probe 100, or may be used to discriminate a state of internal tissues of a human body using High Intensity Focused Ultrasound (HIFU) or the like such that it can be recognized whether abnormal tissues are completely cured or not through the discriminated state of internal tissues.

Generally, there may occur a difference between an abnormal tissue and a normal tissue, and it is well known to those skilled in the art that the abnormal tissue can be discriminated from the normal tissues by analyzing the difference. Therefore, abnormal tissues such as a cancer or tumor may have higher elasticity than normal tissues. As a result, since the abnormal tissues such as a cancer or tumor have higher elasticity than peripheral normal tissues, the abnormal tissues may have higher shear modulus (or higher elastic coefficient). In addition, even when tissues are necrotized using medical ultrasonic waves such as HIFU, the degree of tissue necrosis becomes higher, resulting in higher elasticity in tissues. That is, a state change of tissues may be considered to be a change of tissue elasticity. Therefore, assuming that the degree of tissue elasticity can be recognized using ultrasonic signals, although the doctor does not directly view internal tissues of a human body of a patient, the doctor may non-invasively monitor a state of the internal tissues.

A method for analyzing elasticity of tissues using the ultrasonic probe 100 is applied to a system for assisting medical image diagnosis of doctors who work in hospitals, and may provide the doctors with the result of analyzing the degree of tissue elasticity using ultrasonic images, such that the analyzing method may be utilized for disease diagnosis, medical treatment planning, treatment progress evaluation, etc. The method for analyzing tissue elasticity using the ultrasonic probe 100 may be achieved by acquiring numerical elastic data using shear waves, and all data acquired using shear waves will hereinafter be referred to as shear wave data.

The ultrasonic probe configured to acquire shear wave data will hereinafter be given.

In this case, although a target object (ob) may be a living body of a human or an animal, and a target site may be tissue in the living body, such as blood vessels, bones, muscles, or the like, the scope or spirit of the present invention is not limited thereto. If necessary, all kinds of objects, internal structures of which can be imaged by the ultrasonic imaging apparatus 10, may be used as the target object without departing from the scope or spirit of the present invention.

Prior to analyzing elasticity, the ultrasonic probe 100 may irradiate a ROI (Region of Interest) region of the target object with ultrasonic waves for diagnosis, resulting in occurrence of shear waves. In order to quantitatively analyze the degree of elasticity using diagnostic ultrasound, Acoustic Radiation Force Impulse (ARFI) such as diagnostic ultrasound needs to be pre-applied to the interior of a human body so as to cause displacement of tissues. As described above, shear waves are introduced into tissues due to ARFI, resulting in occurrence of tissue displacement.

Figure 3:
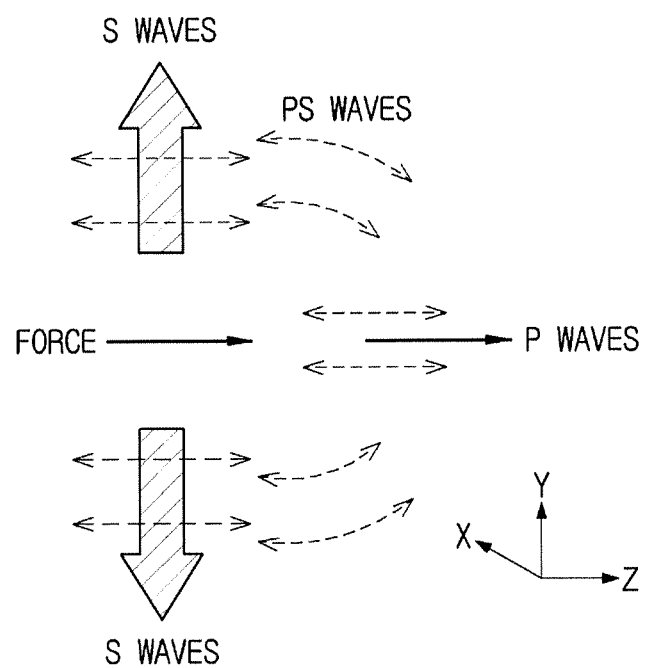
FIG. 3 is a conceptual diagram illustrating shear waves.

FIG. 3 is a conceptual diagram illustrating shear waves. Referring to FIG. 3, assuming that force of a point pulse is applied in a Z-axis direction, P waves indicating longitudinal waves, S waves indicating transverse waves, and PS waves indicating a combination of P and S waves are generated. Here, shear waves may vibrate in a progress direction of fluctuations from a vibration source to which force is applied, and may proceed in a Y-axis direction. The shear waves may refer to S waves.

As force of the point impulse to induce shear waves, the following embodiment of the present disclosure assumes that diagnostic ultrasound of the ultrasonic probe 100 is used. However, the scope or spirit of the present disclosure is not limited thereto, and a medical ultrasonic imaging apparatus such as the HIFU device located outside the ultrasonic imaging apparatus 10, or a vibrator may also be used to induce shear waves. That is, the scope or spirit of a portion for introducing shear waves into the ROI region is not limited thereto, and various portions for introducing such shear waves can be used without departing from the scope or spirit of the present disclosure, as well known to those skilled in the art.

The ultrasonic probe 100 may irradiate diagnostic ultrasound or the like in a depth-axis direction in a manner that a focal point is formed at the ROI region of the target object, such that shear waves may occur in the ROI region.

The ultrasonic probe 100 may acquire shear wave data from the ROI region of a target object (ob) using shear waves derived from the ROI region of the target object (ob). That is, the ultrasonic probe may acquire a plurality of shear wave data segments of the target object.

Shear wave data may refer to elastic data of a target object by detecting shear waves acquired when vibration force is applied to the target object. In addition, shear wave data may include not only a numerical value of elastic data but also broad-sense data. That is, shear wave data may be defined as all data capable of being acquired using shear waves. Therefore, shear wave data may include not only position information of the ROI region of the target object (ob) but also numerical elastic data corresponding to the position information of the ROI region of the target object (ob) acquired using shear waves.

However, the scope or spirit of the present disclosure is not limited thereto, and the ultrasonic probe 100 may acquire not only shear wave data but also various other data capable of being measured using ultrasonic waves.

The ultrasonic probe 100 may include a transducer module 110, a male connector 130, and a cable 120. The transducer module 110 may be contained in a housing (h), may irradiate a target object (ob) with ultrasonic waves, may receive echo ultrasonic waves reflected from the target object (ob), and may perform conversion between an electrical signal and ultrasonic waves. The male connector 130 may be physically connected to a female connector of the main body 200, and may transmit and receive signals to and from the main body 200. The cable 120 may connect the male connector 130 to the transducer module 110. In addition, the ultrasonic probe 100 may be connected to at least one of the main body 200 and the external device over a wireless communication network, and may receive various signals needed to control the ultrasonic probe 100 or may transmit analog or digital signals corresponding to the echo ultrasonic signal received by the ultrasonic probe 100.

Meanwhile, a wireless communication network may be a communication network configured to support a wireless communication scheme capable of wirelessly transmitting and receiving signals. For example, the wireless communication scheme may include not only a communication scheme (e.g., 3G or 4G communication) for transmitting and receiving radio frequency (RF) signals through a base station (BS), but also all direct communication schemes in which RF signals can be directly communicated between devices located within a predetermined distance. For example, the direct communication schemes may include Wireless LAN, Wi-Fi, Bluetooth, ZigBee, Wi-Fi Direct (WFD), Ultra wideband (UWB), Infrared Data Association (IrDA), Bluetooth Low Energy (BLE), Near Field Communication (NFC), etc. without being limited thereto. However, the scope or spirit of the wireless communication schemes is not limited thereto, and may include all kinds of communication networks capable of supporting RF communication between the ultrasonic probe 100 and the main body 200.

An echo ultrasonic signal may be reflected from the target object (ob) to which ultrasonic waves are radiated, and may have various frequency bands or various energy strengths to generate various ultrasonic images according to diagnostic modes.

The transducer module 110 may generate ultrasonic waves or ultrasonic signals according to received AC power. In more detail, the transducer module 110 may receive AC power from an external power-supply device or an internal device (e.g., a battery). A vibrator of the transducer module 110 may vibrate according to the received AC power, and may thus generate ultrasonic waves.

Three directions perpendicular to one another on the basis of the center point of the transducer module 110 may be defined as an axis direction A, a lateral direction L, and an elevation direction E. In more detail, a direction of ultrasonic irradiation is defined as the axis direction A, a direction along which the transducer module 110 forms a column is defined as the lateral direction L, and the remaining direction perpendicular to the directions A and L may be defined as the elevation direction E.

One end of the cable 120 may be connected to the transducer module 110, and the other end of the cable 120 may be connected to the male connector 130, such that the transducer module 110 may be connected to the male connector 130.

The male connector 130 may be connected to the other end of the cable 120, such that the male connector 130 may be physically coupled to the female connector 201 of the main body 200.

The male connector 130 may transmit an electrical signal generated by the transducer module 110 to the female connector 201 physically coupled thereto, or may receive a control signal generated by the main body 200 from the female connector 201.

However, if the ultrasonic probe 100 is implemented as a wireless ultrasonic probe 100, the cable 120 and the male connector 130 may be omitted, and the ultrasonic probe 100 and the main body 200 may communicate with each other through a separate wireless communication module (not shown) contained in the ultrasonic probe 100, without being limited to the ultrasonic probe 100 of FIG. 1.

The main body 200 may communicate with the ultrasonic probe 100 through at least one of a local area network (LAN) communication module and a mobile communication module.

The LAN communication module may denote a communication module for short-range communication within a predetermined distance. The LAN communication technology may include Wireless LAN, Wi-Fi, Bluetooth, ZigBee, Wi-Fi Direct (WFD), Ultra wideband (UWB), Infrared Data Association (IrDA), Bluetooth Low Energy (BLE), Near Field Communication (NFC), etc. without being limited thereto.

The mobile communication module may transmit and receive radio frequency (RF) signals to and from at least one of a base station (BS), an external terminal, and a server over the mobile communication network. In this case, the RF signal may include various types of data. That is, the main body 200 may transmit and receive signals including various types of data to and from the ultrasonic probe 100 through at least one of the base station (BS) and the server.

For example, the main body 200 may transmit and receive signals including various types of data to and from the ultrasonic probe 100 through the base station (BS) over a mobile communication network such as a 3G or 4G network. The main body 200 may communicate with a hospital server or other in-hospital medical machines connected through a Picture Archiving and Communication System (PACS). In addition, the main body 200 may perform data communication according to medical digital imaging and Digital Imaging and Communications in Medicine (DICOM) standard, without being limited thereto.

Besides, the main body 200 may communicate with the ultrasonic probe 100 over a wired communication network.

The wired communication network may be a communication network through which signals may be transmitted and received by wire. In accordance with one embodiment, the main body 200 may communicate with the ultrasonic probe 100 over a wired communication network, for example, Peripheral Component Interconnect (PCI), PCI-express, Universe Serial Bus (USB), etc., without being limited thereto.

The ultrasonic probe will hereinafter be given with reference to the attached drawings.

Figure 4:
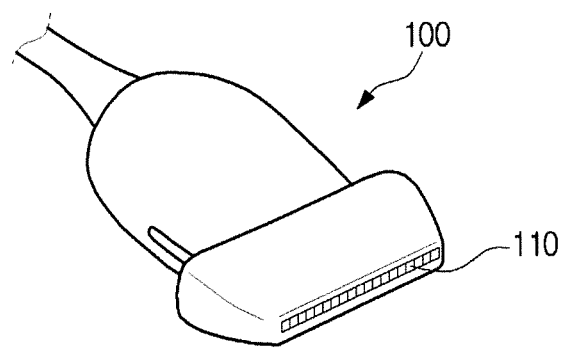
FIG. 4 is a view illustrating an ultrasonic probe including a one-dimensional (1D) array transducer.
Figure 5:
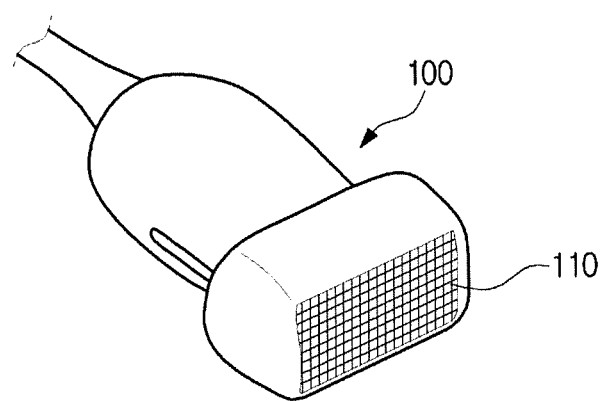
FIG. 5 is a view illustrating an ultrasonic probe including a two-dimensional (2D) array transducer.

FIG. 4 is a view illustrating an ultrasonic probe including a one-dimensional (1D) array transducer. FIG. 5 is a view illustrating an ultrasonic probe including a two-dimensional (2D) array transducer.

Referring to FIGS. 4 and 5, the ultrasonic probe 100 may contact the surface of a target object, and may transmit and receive ultrasonic signals to and from the target object. In more detail, the ultrasonic probe 100 may transmit an ultrasonic signal to a target site contained in the target object according to a transmission signal received from the main body, may receive the echo ultrasonic signal reflected from the target site, and may transmit the received echo ultrasonic signal to the main body. In this case, although the echo ultrasonic signal may be an ultrasonic signal acting as a radio frequency (RF) signal reflected from the target object, the scope or spirit of the echo ultrasonic signal is not limited thereto, and the echo ultrasonic signal may include all kinds of signals obtained by reflection of the ultrasonic signal transmitted to the target object.

Meanwhile, the target object may be a living body of a human or an animal, without being limited thereto. If necessary, all kinds of objects, internal structures of which can be imaged by ultrasonic signals, may be used as the target object without departing from the scope or spirit of the present invention.

The ultrasonic probe 100 may include a transducer array for converting an electrical signal into an ultrasonic signal and vice versa to transmit ultrasonic signals to the interior of the target object. The transducer array may include one or more transducer elements.

The ultrasonic probe 100 may generate an ultrasonic signal through the transducer array, may transmit the ultrasonic signal to a target site contained in the target object, and may receive the echo ultrasonic signal reflected from the target site through the transducer array.

If the echo ultrasonic signal arrives at the transducer array, the transducer array may vibrate at a predetermined frequency corresponding to a frequency of the echo ultrasonic signal, and may output an AC current having a frequency corresponding to a vibration frequency of the transducer array. Therefore, the transducer array may convert the received echo ultrasonic signal into an echo signal indicating a predetermined electrical signal.

Meanwhile, the transducer array may be a 1D array or a 2D array. In accordance with one embodiment, the transducer module 110 may include the 1D transducer array as shown in FIG. 1.

Respective transducer elements constructing the 1D transducer array may convert ultrasonic signals into electric signals and vice versa. For this purpose, the transducer element may include a magnetostrictive ultrasonic transducer using magnetostrictive effects of a magnetic material, a piezoelectric ultrasonic transducer using piezoelectric effects of a material, and a piezoelectric micromachined ultrasonic transducer (pMUT). If necessary, the transducer element may also include a capacitive micromachined ultrasonic transducer (cMUT) to transmit and receive ultrasonic waves using vibration of several hundred or several thousand micromachined thin films.

Meanwhile, the transducer module 110 may be arranged in a linear shape as shown in FIG. 4, or may also be arranged in a convex shape as necessary. The linear-shaped transducer module and the convex-shaped transducer module have the same basic operation principles in the ultrasonic probe 100. However, in the case of using the ultrasonic probe 100 including the convex-shaped transducer module 110, the ultrasonic signal emitted from the transducer module 110 is formed in a fan shape, such that an ultrasonic image to be generated may also be formed in a fan shape.

In another example, the transducer module 110 may include a 2D transducer array as shown in FIG. 5. If the transducer module 110 includes the 2D transducer array, the interior of the target object may be 3D-imaged. Although the transducer array of the ultrasonic probe 100 is one-dimensionally arranged, the ultrasonic probe 100 may acquire volume information of the interior of the target object by mechanically moving the 1D transducer array, the ultrasonic probe 100 may transmit the echo ultrasonic signal capable of generating a three-dimensional (3D) ultrasonic image to the main body 200.

The respective transducer elements constructing the 2D transducer array are identical to the transducer elements constructing the 1D transducer array, and as such a detailed description thereof will herein be omitted for convenience of description. The ultrasonic probe, the ultrasonic imaging apparatus including the same, and internal constituent elements of the ultrasonic imaging apparatus according to the embodiments will hereinafter be given with reference to the attached drawings.

Figure 6:
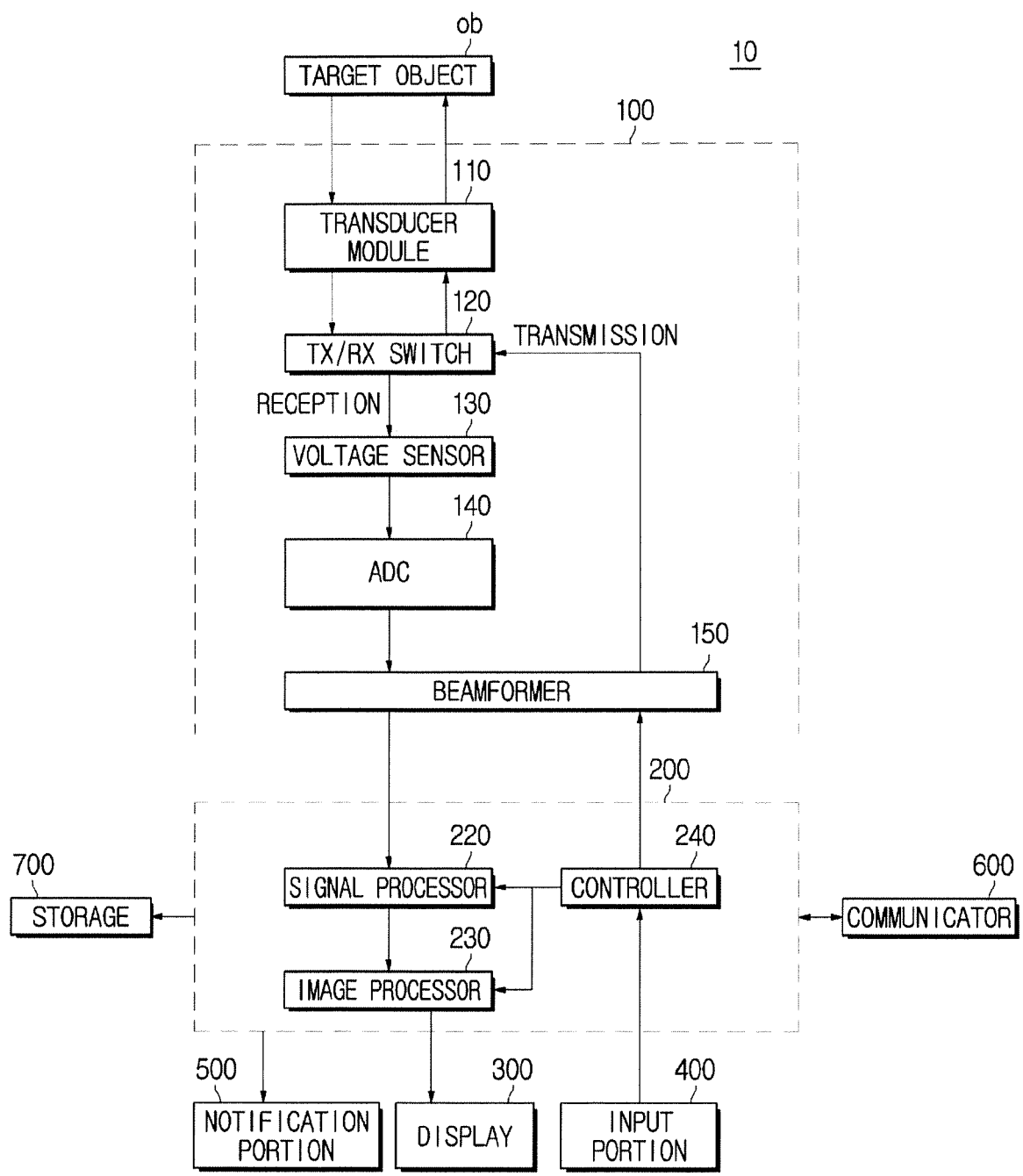
FIG. 6 is a block diagram illustrating an ultrasonic imaging apparatus.

FIG. 6 is a block diagram illustrating the ultrasonic imaging apparatus.

Referring to FIG. 6, the ultrasonic probe 100 may further include a beamformer 150, a transmission/reception (Tx/Rx) switch 120, a voltage sensor 130, and an Analog-to-Digital Converter (ADC) 140, which are contained in the housing (h).

Upon receiving a control signal of a system controller 240, the Tx/Rx switch 120 may change a current mode to a transmission (Tx) mode during ultrasound irradiation, or may change a current mode a reception (Rx) mode during ultrasound reception.

The voltage sensor 130 may detect an output current of the transducer module 110. For example, the voltage sensor 130 may be implemented as an amplifier for amplifying a voltage according to the detected output current.

In addition, the voltage sensor 130 may further include a pre-amplifier configured to amplify a minute analog signal. A low noise amplifier (LNA) may be used as the pre-amplifier.

The voltage sensor 130 may further include a variable gain amplifier (VGA) (not shown) configured to control a gain value according to an input signal. In this case, although a time gain compensation (TGC) circuit configured to compensate for either a gain according to a focus point or a gain according to a distance to the focus point may be used as a VGA, the scope or spirit of the present disclosure is not limited thereto.

The ADC 140 may convert an analog voltage generated from the voltage sensor 130 into a digital signal.

Although FIG. 6 exemplarily illustrates that the digital signal generated from the ADC 140 is input to a beamformer 150 for convenience of description, it should be noted that an analog signal delayed by the beamformer 150 may also be input to the ADC 140 such that the input order of analog and digital signals is not limited thereto.

Although FIG. 6 exemplarily illustrates the ADC 140 installed in the ultrasonic probe 100, the scope or spirit of the present disclosure is not limited thereto, and the ADC 140 may also be installed in the main body 200 as necessary. In this case, the ADC 140 may convert an analog signal focused by an adder into a digital signal.

The beamformer 150 may focus ultrasonic signals generated from the transducer module 110 onto a single target point of the target object (ob) at the same time as desired by the ultrasonic signals generated from the transducer module 110, or may allocate a proper delay time to radiated ultrasonic signals or received echo ultrasonic signals in a manner that the echo ultrasonic signals reflected from the single target point of the target object (ob) arrive at the transducer module 110.

In the ultrasonic imaging apparatus 10 of FIG. 6, the beamformer 150 may be contained in the ultrasonic probe 100 corresponding to a front end as described above, or may be contained in the main body 200 corresponding to a back end. However, the scope or spirit of the beamformer 150 according to the embodiment is not limited thereto, and it should be noted that all or some constituent elements of the beamformer 150 may be contained in the front end or the back end without departing from the scope or spirit of the present disclosure.

The main body 200 may include various constituent elements needed to control the ultrasonic probe 100 or to generate an ultrasonic image on the basis of the signal received from the ultrasonic probe 100, and may be connected to the ultrasonic probe 100 through the cable 120.

In addition, the ultrasonic probe 100 may include one or more processors. Therefore, the ultrasonic probe 100 may include at least one processor acting as the controller contained in the main body 200, and may also be controlled in a different way from the controller 240 of the ultrasonic imaging apparatus 10.

Not only a signal processor 220, an image processor 230, and a controller 240 contained in the main body 200, but also a display 300, an input portion 400, a notification portion 500, a communicator 600, and a storage 700 will hereinafter be given with reference to the attached drawings. In addition, the main body 200 may further include the display 300, the input portion 400, the notification portion 500, the communicator 600, and the storage 700, or may be constructed independently. If the above-mentioned constituent elements of the latter case are identical in structure to those of the former case, a detailed description thereof will herein be omitted for convenience of description.

The signal processor 220 may convert a focused digital signal received from the ultrasonic probe 100 into a signal appropriate for image processing. For example, the signal processor 220 may perform filtering to remove a noise signal other than a desired frequency band.

The signal processor 220 may be implemented as a Digital Signal Processor (DSP), and may generate ultrasonic image data by performing envelope detection processing for detecting the magnitude of an echo ultrasonic signal on the basis of the focused digital signal.

The image processor 230 may generate an image on the basis of the ultrasonic image data generated by the signal processor 220, such that a user (e.g., a doctor or a patient) may view the generated image regarding the interior of the target object (ob) (e.g., a human body).

The image processor 230 may transmit the generated ultrasonic image to the display 300 using the ultrasonic image data.

In accordance with the embodiment, the image processor 230 may perform additional image processing for the ultrasonic image as necessary. The image processor 230 may further perform post-processing of the ultrasonic image. As an example of the post-processing, the image processor 230 may correct or readjust contrast, brightness, and sharpness of the ultrasonic image.

The additional image processing of the image processor 230 may be carried out according to predetermined setting information, or may be carried out by a user instruction or command received through the input portion 400.

The controller 240 may control at least one of the ultrasonic imaging apparatus 10 and the ultrasonic probe 100. For example, the controller 240 may control the signal processor 220, the image processor 230, the ultrasonic probe 100, and the display 300.

In addition, the controller 240 may perform grouping of plural shear wave data acquired by the ultrasonic probe 100 according to a predetermined condition, and may thus determine at least one shear wave data group.

Here, the predetermined condition may include at least one of a user-desired ROI (Region of Interest) region, a portion of a target object, the category of ultrasonic images, and the position of ultrasonic images. In addition, the scope or spirit of the predetermined condition is not limited thereto, and the predetermined condition may also be changed according to user setting information. The predetermined condition may also be determined to be another data different from the above-mentioned description. For example, assuming that the predetermined condition is set to a specific position at which shear wave data contained in an error range is acquired according to the result of comparison between the predetermined condition and shear wave data acquired by the ultrasonic probe 100, the controller 240 may perform grouping of shear wave data corresponding to all the positions capable of satisfying the above condition, and may determine the grouped shear wave data to be a single shear wave data group.

Therefore, the controller 240 may classify the acquired data and perform grouping of the classified data according to the above-mentioned conditions. Although the above-mentioned example has been disclosed using shear wave data as an example, the scope or spirit of the present disclosure may also be applied to various data types other than the shear wave data.

The controller 240 may perform grouping of the plurality of shear wave data configured to satisfy a predetermined condition according to a user manipulation or a predetermined instruction, such that the controller 240 may determine at least one shear wave data group.

Here, grouping of the plurality of shear wave data according to the user manipulation may indicate that the above-mentioned condition is satisfied and the user can set shear wave data directly selected through the input portion 400 to each shear wave data group. That is, the user may manually bind the plurality of shear wave data through the input portion such that the plurality of shear wave data can be grouped into a shear wave data group.

In addition, grouping of the plurality of shear wave data according to a predetermined condition may indicate that the above-mentioned condition is satisfied, a plurality of shear wave data segments may be classified according to a condition stored in the processor contained in the controller 240, the classified shear wave data segments may be set to a plurality of shear wave data groups. That is, the plurality of shear wave data segments may be automatically combined by the controller, such that the resultant shear wave data segments can be grouped into a shear wave data group.

In addition, the controller 240 may transmit an electrical signal indicating information regarding at least one shear wave data group determined by grouping the plurality of shear wave data segments acquired by the ultrasonic probe 100 according to a predetermined condition, to the display 300.

The display 300 may display various kinds of information received from the controller 240. In addition, the display 300 may display information regarding the shear wave data group received from the controller 240, as at least one image. A detailed description thereof will hereinafter be described.

In accordance with one embodiment, the controller 240 may control the ultrasonic imaging apparatus 10 according to the predetermined setting information, or may generate a predetermined control command according to a user instruction or command received through the input portion 400 and may then control the ultrasonic imaging apparatus 10.

The controller 240 may control not only the ultrasonic imaging apparatus 10 but also the ultrasonic probe 100. If the controller 240 is paired with the external device using wireless communication, Bluetooth, NFC, IrDA, etc. the controller 240 may control at least one of the ultrasonic imaging apparatus 10 and the ultrasonic probe 100 through the external device. In addition, the controller 240 may control the communicator 600 to transmit various kinds of information regarding the ultrasonic imaging apparatus 10 to the external device.

The controller 240 may include a read only memory (ROM) and a random access memory (RAM). The ROM may store control programs for controlling the processor and ultrasonic imaging apparatus 10 therein. The RAM may store signals or ultrasonic image data received from either the ultrasonic probe 100 or the input portion 400 of the ultrasonic imaging apparatus 10, or may be used as a storage region corresponding to various tasks executed by the ultrasonic imaging apparatus 10. In addition, although the controller 240 of the embodiment is contained in the main body 200, the scope or spirit of the present disclosure is not limited thereto, and the controller 240 may also be contained in the ultrasonic probe 100 as necessary. The controller 240 may include one or more processors.

A separate circuit board electrically coupled to the controller 240 may include a graphic processing board including a processor and a RAM or ROM.

The processor, the RAM, and the ROM may be coupled to one another through an internal bus.

The controller 240 may refer to a term indicating a constituent element including the processor, the RAM, and the ROM.

The processor 240 may refer to a term indicating a constituent element including the processor, the RAM, the ROM, and the processing board.

The display 300 may display an ultrasonic image generated by the image processor 230 in such a manner that the user may visually recognize the internal structure or tissues of the target object (ob). The display 300 may simultaneously display shear wave data acquired by the ultrasonic probe 100 and an ultrasonic image. The display 300 may display various data and images in association with the ultrasonic imaging apparatus 10.

In addition, the display 300 may display at least one image corresponding to at leas one shear wave data group decided by the controller 240. The display 300 may also display the plurality of shear wave data at different positions from the image display position. The display 300 may selectively display at least one image corresponding to at least one shear wave data group. For example, if the user inputs a command for selecting at least one of the plurality of images through the input portion 400, the display 300 may selectively display at least one image corresponding to at least one shear wave data group. In other words, the display 300 may display at least one of plural images and plural shear wave data groups selected by the input portion 400. A detailed description thereof will hereinafter be given with reference to the attached drawings.

In more detail, the display 300 may simultaneously display not only the internal structure or tissues of the target object (ob) but also elasticity of the region of interest (ROI) of the target object (ob), such that the user may visually recognize images of the target object (ob) and may numerically confirm the images of the target object (ob).

The display 300 may be implemented by any well-known display panel, for example, a Cathode Ray Tube (CRT), a Liquid Crystal Display (LCD), a Light Emitting Diode (LED), a Plasma Display Panel (PDP), an Organic Light Emitting Diode (OLED), etc., without being limited thereto.

If the display 300 is implemented as a touchscreen, the display 300 may also act as the input portion 400. That is, the main body 200 may receive various commands from the user through at least one of the display 300 and the input portion 400.

If the display 300 is used as the input portion 400, the display 300 may display at least one of a UI (User Interface) screen image and a selection screen image through which the user can input a command. In this case, the user may touch at least one of an icon, an image, and text displayed on the display 300, such that the corresponding function of at least one of the ultrasonic imaging apparatus 10 and the ultrasonic probe 100 can be carried out.

In more detail, if the display 300 acts as a touchscreen, the display 300 may display at least one of an icon, an image, and text, which are needed to add annotation or comments to ultrasonic images and measurement data, as well as to perform focusing, TGC/LGC control, zoom-in/zoom-out, rotation, 2D/3D conversion, etc. of the ultrasonic images and measurement data.

In this case, since the display 300 includes the touchscreen function, the user may select at least one of an icon, an image, and text displayed on the display 300 in a manner that the ultrasonic imaging apparatus 10's function corresponding to at least one of the icon, image, and text can be carried out.

Although not shown in the drawings, the main body 200 may include a voice recognition sensor such that the main body 200 may receive a voice command from the user through the voice recognition sensor.

The input portion 400 may receive not only the setting information related to the ultrasonic probe 100 but also various control commands from the user. In addition, the input portion 400 may receive at least one of a selection command, a cancel command, a deletion command, and an editing command of at least one image corresponding to at least one shear wave data group displayed on the display 300.

The input portion 400 may receive a command for adding annotation or comments to at least one image displayed on the display 300. The input portion 400 may receive at least one of a command for performing various operations of the ultrasonic imaging apparatus 10 and the other command for changing the setting information related to the ultrasonic probe 100.

In accordance with one embodiment, the setting information related to the ultrasonic probe 100 may include gain information, zoom information, focus information, TGC information, depth information, frequency information, power information, frame average information, dynamic range information, etc. However, the setting information related to the ultrasonic probe 100 is not limited thereto, and may include various kinds of information capable of being established to capture ultrasonic images.

The above-mentioned information may be transferred to the ultrasonic probe 100 over a wired or wireless communication network, and the ultrasonic probe 100 may be established according to the received information. The main body 200 may receive various control commands (e.g., a command for transmitting the ultrasonic signal) from the user through the input portion 400, and may transmit the received control commands to the ultrasonic probe 100.

Meanwhile, the input portion 400 may also be implemented as a mouse, a keyboard, a foot switch, or a foot pedal. For example, the keyboard may be implemented by hardware. The keyboard may include at least one of a switch, a key, a joystick, a trackball, etc. In another example, the keyboard may also be implemented by software such as a graphical user interface (GUI). In this case, the keyboard may be displayed on the display 300. The foot switch or the foot pedal may be located below the main body 200, and the user may control the ultrasonic imaging apparatus 10 using the foot pedal.

One or more female connectors 201 (see FIG. 1) may be contained in the main body 200, and the female connector 201 may be connected to the ultrasonic probe 100 through the cable 120 and the male connector 130.

Upon receiving at least one of a control command and various kinds of information from the controller 240, the display 300 may display information corresponding to the received information.

The display 300 may receive various kinds of information and a control command from the ultrasonic probe 100, and may display information corresponding to the received information.

In addition, the display 300 may display various kinds of data acquired by the ultrasonic probe 100 in various shapes.

In more detail, the display 300 may output a plurality of shear wave data segments acquired by the ultrasonic probe 100 in the form of a list. The display 300 may also output the plurality of shear wave data segments acquired by the ultrasonic probe in the form of an image.

The display 300 may display at least one image corresponding to at least one shear wave data group decided by the controller 300.

In this case, at least one image may conceptually include all kinds of things capable of being visually distinguished from one another using at least one of a symbol, a letter, a figure, a shape, a color, and a 3D structure. In addition, the display may also display numerical values of the plurality of shear wave data segments using at least one of a symbol, a letter, a figure, a shape, a color, and a 3D structure in such a manner that the numerical values can be visually distinguished from one another.

Therefore, the user may easily identify the shear wave data group decided by the controller 240 through a plurality of images displayed on the display 300. In addition, the user may also easily identify each shear wave data contained in the shear wave data group.

In addition, if at least one image corresponding to at least one shear wave data group is selected by the input portion 400, the display 300 may rearrange plurality of shear wave data belonging to the selected image and display the rearranged shear wave data.

In this case, rearrangement may be achieved according to a predetermined reference. For example, the plurality of shear wave data segments may be rearranged according to various references, for example, the order of acquisition times, the descending numerical order, the ascending numerical order, and the position of a target object, etc. Therefore, the shear wave data segments are arranged and displayed on the display 300, such that the user may more easily compare and observe the shear wave data.

If at least one image corresponding to at least one shear wave data group is selected by the input portion 400, the display 300 may display the plurality of shear wave data segments at a peripheral position of the selected image using at least one of an icon, a text, and an image.

In addition, the display 300 may also display the plurality of shear wave data segments at different positions from the image display position. The display 300 may selectively display at least one image corresponding to at least one shear wave data group decided by the controller 300.

The display 300 may display an ultrasonic image regarding a target site contained in the target object. The ultrasonic image displayed on the display 300 may be a 2D ultrasonic image or a 3D ultrasonic image, and may display various ultrasonic images according to operation modes of the ultrasonic imaging apparatus 10. The display 300 may display not only menus or information needed for ultrasound diagnosis but also information regarding operation states of the ultrasonic probe 100.

In accordance with one embodiment, the ultrasonic image may include an amplitude mode (A-mode) image, a brightness mode (B-mode) image, a motion mode (M-mode) image, a color mode (C-mode) image, and a Doppler mode (D-mode) image.

The A-mode image may refer to an ultrasonic image indicating the amplitude of an ultrasonic signal corresponding to an echo ultrasonic signal. The B-mode image may refer to an ultrasonic image in which the amplitude of the ultrasonic signal corresponding to the echo ultrasonic signal is represented as brightness. The M-mode image may refer to an ultrasonic image indicating movement of a target object according to lapse of time at a specific position. The D-mode image may refer to an ultrasonic image in which a moving target object is represented as a waveform shape using the Doppler effect. The C-mode image may refer to an ultrasonic image for indicating the moving target object using a color spectrum.

The input portion 400 may receive an instruction or command from the user so as to control the ultrasonic imaging apparatus 10. For example, the input portion 400 may include a user interface (UI), for example, a keyboard, a mouse, a trackball, a touchscreen, and an input button or paddle mounted to the ultrasonic probe 100.

If at least one image corresponding to at least one shear wave data group displayed on the display is selected through the input portion, the notification portion 500 may inform the user of the selection result. The notification portion 500 may make a distinction among different contacts detected by the contact sensing portion 160, and may inform the user of the different contacts. In more detail, the notification portion 500 may audibly or visually inform the user of specific information as to whether the user contacts the contact sensing portion 160 using at least one of vibration, sound, a symbol, a letter, a figure, and a 3D structure. In addition, the notification portion 500 is contained in the main body 200 so that the notification portion 500 may output notification information through the speaker or the display 300. However, the scope or spirit of the present disclosure is not limited thereto, and the notification portion 500 may also be contained in the ultrasonic probe 100.

The communicator 600 may wirelessly communicate with at least one of the external device and the ultrasonic probe 100. The communicator 600 may transmit and receive data related to target object diagnosis, for example, an ultrasonic image, an echo ultrasonic signal, Doppler data, and shear wave data acquired through the ultrasonic probe 100. The communicator 600 may receive a variety of information from the external device. Here, the external device may include a wearable terminal, a wireless communication terminal, a smartphone, etc. The communicator 600 may also transmit information for displaying at least one image corresponding to at least one shear wave data group to the external device.

The storage 700 may store at least one of an ultrasonic image of a target object acquired by the ultrasonic probe 100, diagnostic data regarding the ultrasonic image, and shear wave data of the target object. The storage 700 may also store various setting items regarding the ultrasonic imaging apparatus 10. The storage 700 may also store a shear wave data group decided by the controller 240. The storage 700 may store an image corresponding to the shear wave data group. The storage 700 may be configured as at least one of a flash memory type, a hard disk type, a multimedia card micro card, a card type memory (e.g. a Secure Digital (SD) memory or an eXtreme Digital (XD) memory), a Random Access Memory (RAM), a Read Only Memory (ROM), an Electrically Erasable Programmable Read Only Memory (EEPROM), a Programmable Read Only Memory (PROM), a magnetic memory, a magnetic disk, an optical disc, etc. without being limited thereto.

Figure 7:
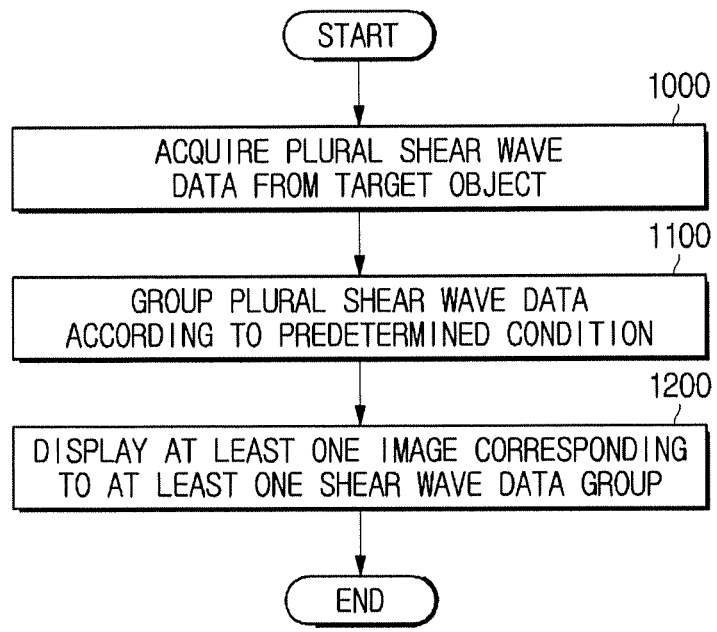
FIG. 7 is a flowchart illustrating a method for grouping a plurality of shear wave data segments and displaying the grouped result as an image using a display.
Figure 9:
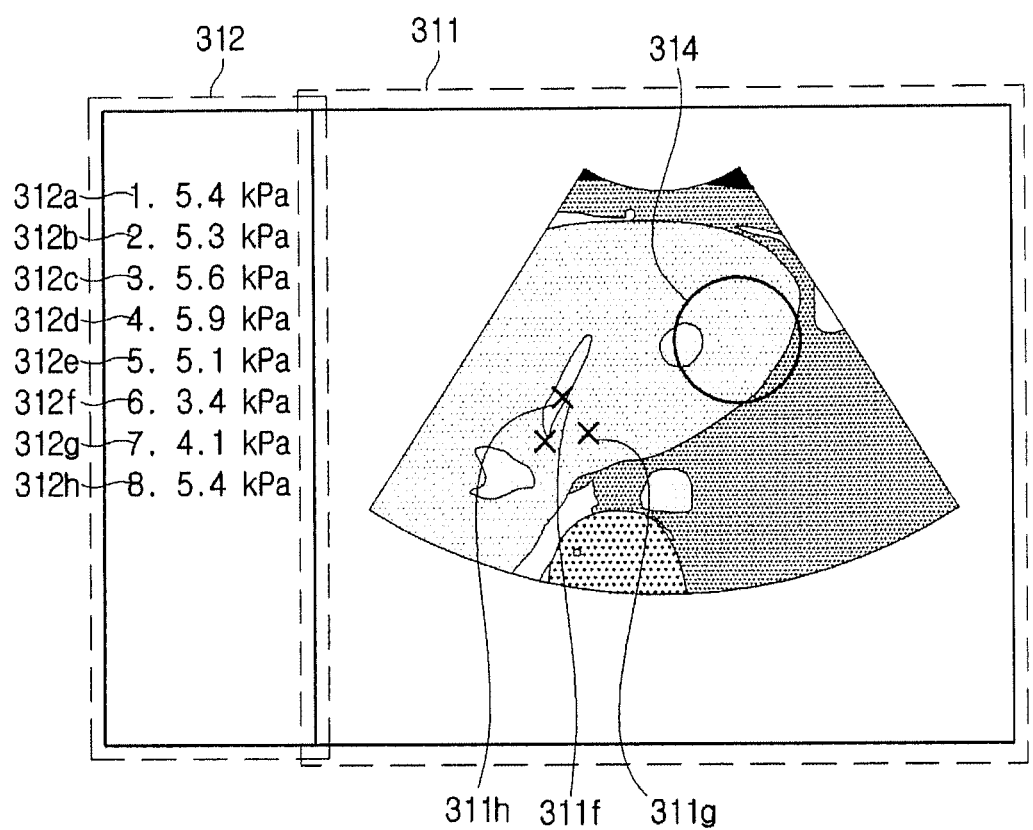
FIG. 9 is a view illustrating an example of an output screen image of the display for displaying a single image by grouping a plurality of shear wave data segments.
Figure 10:
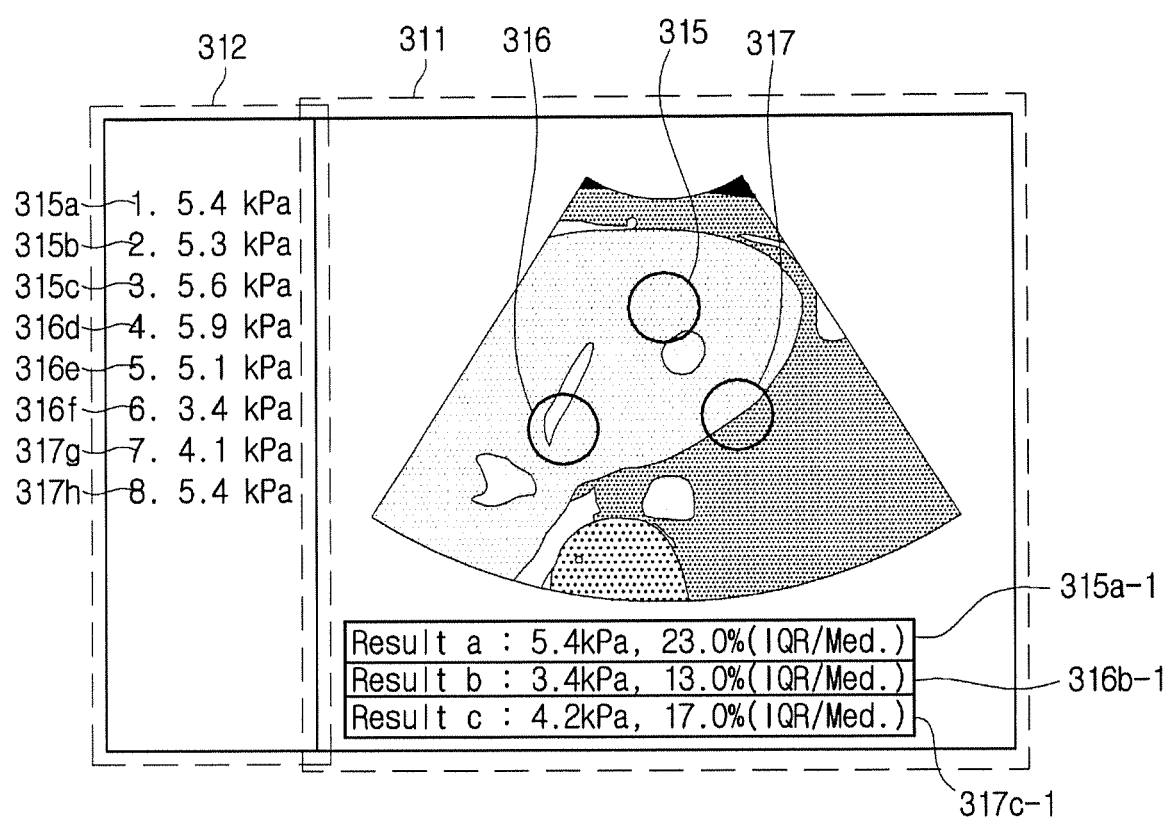
FIG. 10 is a view illustrating an example of various output screen images of the display for displaying a plurality of images by grouping a plurality of shear wave data segments.

FIG. 7 is a flowchart illustrating a method for grouping a plurality of shear wave data segments and displaying the grouped result as an image using a display. FIG. 8 is a view illustrating an example of an output screen image of the display for explaining a process for grouping a plurality of shear wave data segments. FIG. 9 is a view illustrating an example of an output screen image of the display for displaying a single image by grouping a plurality of shear wave data segments. FIG. 10 is a view illustrating an example of various output screen images of the display for displaying a plurality of images by grouping a plurality of shear wave data segments.

A method for acquiring shear wave data, a method for grouping shear wave data, and a method for displaying an image in response to the shear wave data group will hereinafter be given with reference to FIGS. 7 to 10.

Referring to FIG. 7, the ultrasonic probe 100 may acquire shear wave data regarding the ROI region of the target object (Operation 1000).

In this case, the ultrasonic probe 100 may acquire a plurality of shear wave data segments when a plurality of ROI regions of the target object is used. The shear wave data may include position information regarding the ROI region of the target object and a numerical value of elastic data corresponding to the position information of the ROI region of the target object.

If a command for grouping the plurality of shear wave data segments acquired by the ultrasonic probe 100 is input to the controller 240 through the input portion 400, the controller 240 may perform grouping of the plurality of shear wave data segments according to a predetermined condition, and may determine at least one shear wave data group (Operation 1100). The controller 240 may transmit information regarding the determined shear wave data group to the display 300.

The display 300 may receive information regarding the shear wave data group from the controller 240, and may display an image corresponding to at least one shear wave data group decided by the controller 240 (Operation 1200).

If a plurality of shear wave data groups decided by the controller 240 is present, the display 300 may display a plurality of images corresponding to the plurality of shear wave data groups.

The display 300 may display the plurality of shear wave data segments acquired by the ultrasonic probe 100 in various ways.

FIG. 8 illustrates various types of examples for displaying shear wave data.

Referring to FIG. 8, if the ultrasonic probe 100 acquires shear wave data regarding the respective points of the target object, the display 300 may display an ultrasonic image 311 for displaying the respective points of the target object and a list screen image 312 for displaying shear wave data values corresponding to the respective points of the target object.

The ultrasonic image 311 of FIG. 8 shows the respective points of the target object. In more detail, first to eighth display points 311a to 311f may be displayed on the ultrasonic image 311, and may denote the respective points of the target object. In addition, first to eighth shear wave data segments 312a to 312h at the first to eighth display points 311a to 311h may be displayed on the list screen image 312, and the first to eighth shear wave data segments 312a to 312h may respectively correspond to the first to eighth display points 311a to 311h.

That is, the first point 311a of the target object may correspond to the shear wave data segment 312a obtained from the first point 311a. Likewise, the remaining second to eighth points 311b to 311f may also correspond to the second to eighth shear wave data segments 312b to 312h, respectively. However, the points displayed on the ultrasonic image 311 may sequentially correspond to the shear wave data displayed on the list screen image 312 for convenience of description, and the relationship between the points and the shear wave data may also be changed according to user setting information.

The user may combine a plurality of shear wave data segments into one group using various input methods through the input portion 400. The shear wave data group may refer to a bundle of one data acquired when the plurality of shear wave data segments is grouped according to a predetermined condition.

Referring to FIG. 8, for example, assuming that the user desires to combine the first to fifth points 311a to 311e of the target object into a single group, when an associated command is input to the controller 240 through the input portion 400, the controller 240 may determine shear wave data of the first to fifth points 311a to 311e of the target object to be a single shear wave data group 313. In addition, the controller 240 may control the display 300 to display the single determined shear wave data group as a single image corresponding thereto.

Referring to FIG. 9, if the user inputs a command for grouping shear wave data segments of the first to fifth points 311a to 311e of the target object, the display 300 may display an image 314 corresponding to a single shear wave data group including shear wave data segments of the first to fifth points 311a to 311e of the target object. In addition, the display 300 may numerically display the plurality of shear wave data segments on the list screen image 312 located at a different position from the ultrasonic image 311 on which the image 314 is simultaneously displayed.

The display 300 may display at least one image corresponding to at least one shear wave data group, and may display the plurality of shear wave data segments at different positions from the image display position.

A detailed description thereof will hereinafter be given with reference to FIG. 10.

FIG. 10 illustrates an example of the screen image displayed on the display 300. When the user inputs a command for dividing shear wave data into 3 shear wave data groups, the screen image of FIG. 10 may be displayed. However, FIG. 10 is merely an example of the screen image displayed on the display 300, and the scope or spirit of the present disclosure is not limited thereto.

The ultrasonic image 311 from among screen images displayed on the display 300 may include a first image 315, a second image 316, and a third image 317. In addition, the first to eighth shear wave data segments 315a to 317b may be displayed on the list screen image 312 from among the images displayed on the display 300.

In addition, the first to third shear wave data segments 315a to 315c of the list screen image 312 may construct a first shear wave data group, and the fourth to sixth shear wave data segments 316a to 316c of the list screen image 312 may construct a second shear wave data group. Finally, the seventh to eighth shear wave data segments 317a and 317b of the list screen image 312 may construct a third shear wave data group.

Therefore, the display 300 may display the first shear wave data group and the first image 315 to be matched with each other, and the display 300 may display the second shear wave data group and the second image 316 to be matched with each other. In addition, the display 300 may also display the third shear wave data group and the third image 317 to be matched with each other.

An average value 315a-1 of the first to third shear wave data segments, an average value 316b-1 of the fourth to sixth shear wave data segments, and an average value 317c-1 of the seventh to ninth shear wave data segments may be displayed at a lower part of the ultrasonic image 311 from among the images displayed on the display 300.

In addition, the display 300 may also display the first image 315, the second image 316, and the third image 317 to be visually distinguished from one another using at least one of a symbol, a letter, a figure, a shape, a color, and a 3D structure.

For example, the first image may be displayed as a star shape, and the first to third shear wave data segments 315*a* to 315*c* corresponding to the first image 315 may be displayed as red letters. The second image 315 may be displayed as a circular shape, and the fourth to sixth shear wave data segments 316*d* to 316*f* corresponding to the second image 316 may be displayed as yellow letters. The third image 317 may be displayed as a triangular shape, and the seventh to eighth shear wave data segments 317*a* and 317*b* may be displayed as blue letters.

However, the above-mentioned example is merely an example for discriminating between an image displayed on the display 300 and shear wave data, and displaying the image and the shear wave data in different ways, and the scope or spirit of the present disclosure is not limited thereto.

Figure 11:
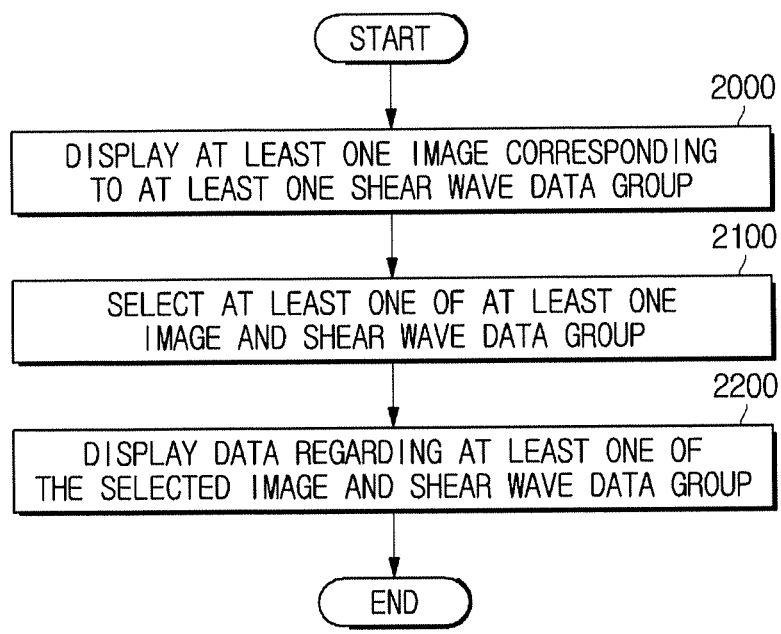
FIG. 11 is a flowchart illustrating a method for displaying an image by grouping a plurality of shear wave data segments and displaying shear wave data on a display upon receiving an image selection command.
Figure 12:
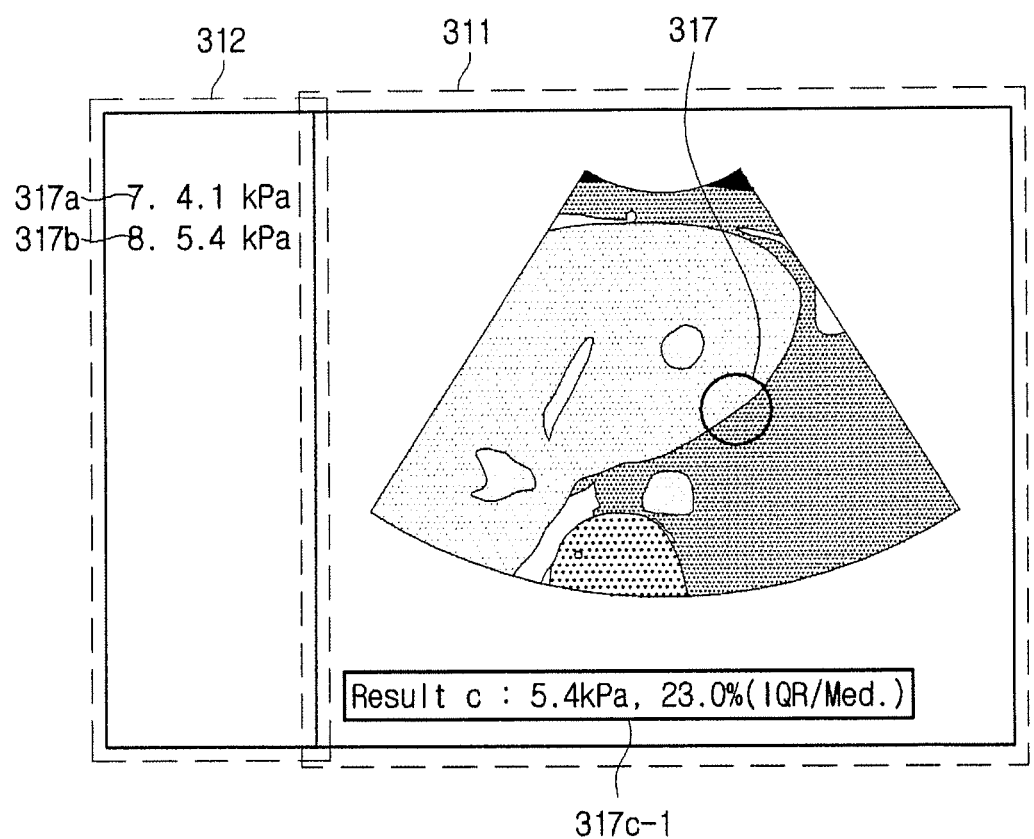
FIG. 12 is a view illustrating an example of a screen image displayed when a plurality of images acquired by grouping plurality of shear wave data segments is selected, deleted, or edited.
Figure 13:
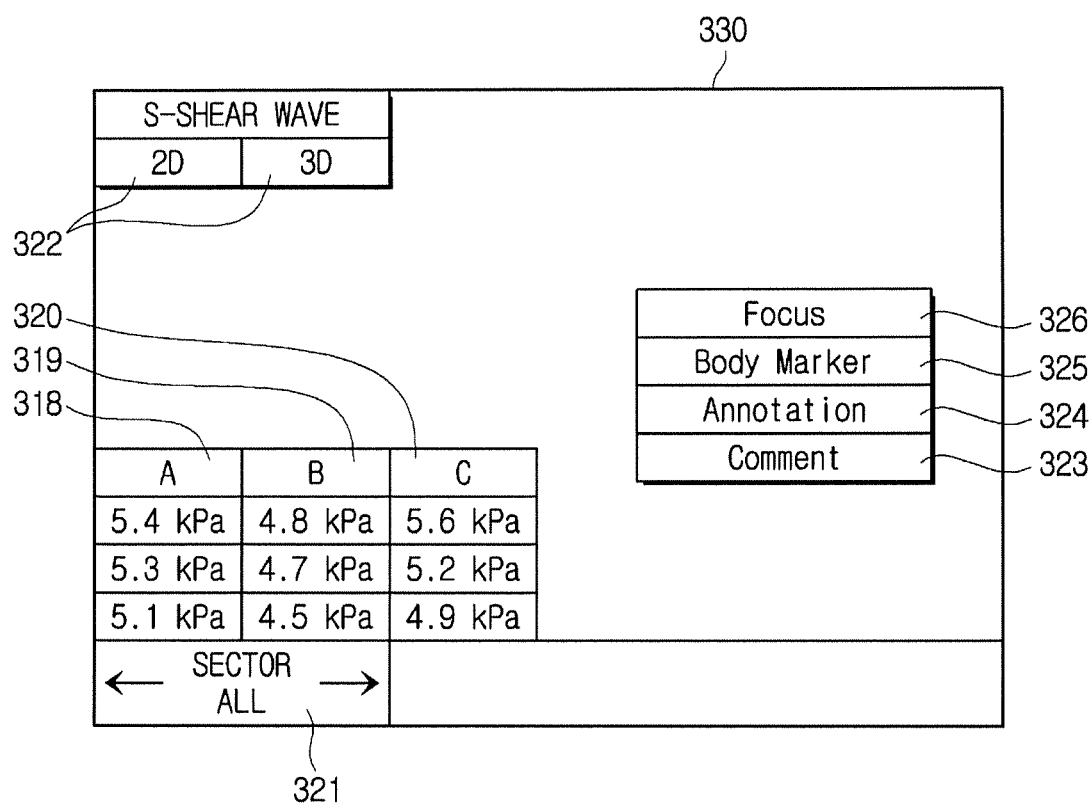
FIG. 13 is a view illustrating an example of an input screen image displayed when a control command is input to an ultrasonic imaging apparatus.

FIG. 11 is a flowchart illustrating a method for displaying an image by grouping a plurality of shear wave data segments and displaying shear wave data on a display upon receiving an image selection command. FIG. 12 is a view illustrating an example of a screen image displayed when a plurality of images acquired by grouping plurality of shear wave data segments is selected, deleted, or edited. FIG. 13 is a view illustrating an example of an input screen image displayed when a control command is input to an ultrasonic imaging apparatus.

The display 300 may display at least one image corresponding to at least one shear wave data group, and the user may select, delete, or edit the image displayed on the display 300 using the input portion 400. In addition, the user may display shear wave data displayed on the display 300 in various ways through the input portion 400. A detailed description thereof will hereinafter be given with reference to FIGS. 11 to 13.

The display 300 may display at least one image corresponding to at least one shear wave data group (Operation 2000).

The input portion 400 may receive a selection command, a deletion command, an editing command, etc. of at least one of the image displayed on the display 300 and the shear wave data group (Operation 2100).

In this case, the input portion 400 may receive commands through various input units. For example, various input units may include at least one of a keyboard, an input button and mouse contained in at least one of the ultrasonic probe 100 and the ultrasonic imaging apparatus 10, the ultrasonic probe 100, and a touchscreen-shaped display 300.

If a command for selecting at least one of the shear wave data group and the plurality of images displayed on the display 300 is input through the above-mentioned input portions, the display 300 may display information selected from among the shear wave data group and the plurality images (Operation 2200).

Referring to FIG. 12, if the user inputs a command for selecting at least one of the third image 317 and the third shear wave data group at the display image of FIG. 10 through various input units, the display 300 may display only information regarding the third image 318 and the third shear wave data group.

For example, the ultrasonic image 311 from among the images displayed on the display 300 may display the third image 317 and an average value 317*c*-1 of the respective shear wave data segments contained in the third shear wave data group. The list screen image 312 from among the images displayed on the display 300 may display the seventh shear wave data 317*a* and the eighth shear wave data 317*b*. However, the above-mentioned example is merely an example obtained when the user selects one of the plurality of images and one of the plurality of shear wave data groups through the input portion 400, and the scope or spirit of the present disclosure is not limited thereto.

FIG. 13 illustrates an example of the input screen image displayed when a control command is input to the ultrasonic imaging apparatus.

When the display 300 is implemented as a touchscreen acting as an input portion, one example of an input screen image 330 displayed on the display 300 is shown in FIG. 13. Not only the input screen image 330 but also the ultrasonic image 311 and the list screen image 312 of FIG. 10 may be simultaneously displayed on the display 300. In addition, if the ultrasonic imaging apparatus 10 includes a plurality of displays 300, the input screen image 330, the ultrasonic image 311, and the list screen image 312 may also be displayed at different displays 300.

An execution icon 322 for converting the ultrasonic image acquired by the ultrasonic probe 100 into a 2D or 3D image may be displayed on the input screen image 330 of the display 300.

The input screen image 330 of the display 300 may display an icon 323 for allowing the user to input a comment to at least one of the ultrasonic image and the shear wave data, an icon 324 for allowing the user to add comments or annotation to the ultrasonic image, an icon 325 for displaying a body marker on the ultrasonic image, and an icon 326 for magnifying (or zooming in on) the ultrasonic image.

In addition, the plurality of shear wave data segments corresponding to the first to third images 315 to 317 may also be displayed in the form of a plurality of lists 318 to 320. The plurality of list shapes 318 to 320 may be selected by the input portion 400. In this case, only the list selected from among the plurality of list shapes 318 to 320 may be displayed. If the plurality of list shapes 318 to 320 is selected by the input portion 400, all the list shapes 318 to 320 may be displayed as shown in FIG. 13.

The display 300 may also display an icon 321 for selecting at least one of the plurality of shear wave data groups and the plurality of images.

However, the screen image displayed on the display 300 is merely an example of the present disclosure, the scope or spirit of the present disclosure is not limited thereto, and the screen image may be displayed using various shapes of user interfaces (UIs).

The ultrasonic imaging apparatus configured to acquire at least one shear wave data group by grouping the acquired shear wave data segments according to a predetermined condition, and to display at least one image corresponding to at least one shear wave data group, and the method for controlling the same have been disclosed above.

As is apparent from the above description, the ultrasonic imaging apparatus and the method for controlling the same according to the embodiments can perform grouping of a plurality of shear wave data segments acquired by an ultrasonic probe, and can display the grouped result as a single image, such that the plurality of shear wave data segments can be easily classified.

The ultrasonic imaging apparatus and the method for controlling the same according to the embodiments can perform grouping of a plurality of shear wave data segments acquired by an ultrasonic probe, and can display a single image, such that the plurality of shear wave data segments can be more easily compared with one another at respective positions of a target object.

The above-mentioned embodiments are merely exemplary for better understanding of the present disclosure, and the scope of the present disclosure is not limited thereto. For example, a single component may be divided into two or more components, or two or more components may be combined into a single component as needed.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic imaging apparatus comprising:
   an ultrasonic probe configured to acquire a plurality of shear wave data segments from a target object;
   a controller configured to determine a first shear wave data group and a second shear wave data group by grouping the plurality of shear wave data segments according to a predetermined condition; and
   a display configured to display a first image corresponding to the first shear wave data group and a second image corresponding to the second shear wave data group to be visually distinguished in a ultrasonic image, and display the plurality of shear wave data segments at positions different from a specific position at which the first and second image are displayed,
   wherein the predetermined condition includes at least one of a Region of Interest (ROI) region, a target site, an image range, or an image position, and
   wherein the first image and the second image are displayed in different positions from each other.

2. The ultrasonic imaging apparatus according to claim 1, wherein the display is configured to selectively display the first image corresponding to the first shear wave data group and the second image corresponding to the second shear wave data group.

3. The ultrasonic imaging apparatus according to claim 1, wherein:
   the controller determine the plurality of shear wave data groups by grouping the plurality of shear wave data segments based on a user manipulation or a predefined instruction.

4. The ultrasonic imaging apparatus according to claim 1, wherein:
   the first image and the second image are visually distinguished from each other using at least one of a symbol, a letter, a figure, a shape, a color, or a solid structure.

5. The ultrasonic imaging apparatus according to claim 1, further comprising:
   an input portion configured to select at least one of the first image corresponding to the first shear wave data group and the second image corresponding to the second shear wave data group.

6. The ultrasonic imaging apparatus according to claim 5, wherein:
   in response to the at least one image being selected through the input portion, the display rearranges the plurality of shear wave data segments belonging to the selected image and displays the rearranged shear wave data segments.

7. The ultrasonic imaging apparatus according to claim 1, further comprising:
   a communicator configured to transmit information corresponding to the plurality of images to an external device.

8. The ultrasonic imaging apparatus according to claim 5, further comprising:
   a notification portion is configured to inform a user of selection result in response to the at least one image being selected through the input portion.

9. A method for controlling an ultrasonic imaging apparatus comprising:
   acquiring a plurality of shear wave data segments from a target object;
   determining a first wave data group and a second shear wave data group by grouping the plurality of shear wave data segments according to a predetermined condition; and
   displaying a first images corresponding to the first shear wave data group and a second image corresponding to the second shear wave data group to be visually distinguished in a ultrasonic image, and display the plurality of shear wave data segments at positions different from a specific position at which the first image and the second image are displayed,
   wherein the predetermined condition includes at least one of a Region of Interest (ROI) region, a target site, an image range, or an image position, and
   wherein the first image and the second image are displayed in different positions from each other.

10. The method according to claim 9, wherein the displaying the plurality of images comprises:
    selectively displaying the first image corresponding to the first shear wave data group and the second image corresponding to the second shear wave data group.

11. The method according to claim 9, wherein the determining the plurality of shear wave data groups comprises:
    determining the plurality of shear wave data groups by grouping the plurality of shear wave data segments based on a user manipulation or a predefined instruction.

12. The method according to claim 9, wherein:
    the first image and the second image are visually distinguished from each other using at least one of a symbol, a letter, a figure, a shape, a color, or a solid structure.

13. The method according to claim 9, further comprising:
    selecting at least of the first image corresponding to the first shear wave data group and the second image corresponding to the second shear wave data group,
    wherein the displaying includes:
    if at least one of the first image corresponding to the first shear wave data groups and the second image corresponding to the second shear wave data group is selected, rearranging the plurality of shear wave data segments belonging to the selected image, and displaying the rearranged shear wave data segments.

14. The method according to claim 13, further comprising, in response to selecting the at least one image corresponding to the at least one shear wave data group, informing a user of the selection result.

15. The method according to claim 9, further comprising transmitting information needed to display the at least one image corresponding to the at least one shear wave data group to an external device.

* * * * *